US008022027B2

(12) United States Patent
Souter et al.

(10) Patent No.: US 8,022,027 B2

(45) **Date of Patent: *Sep. 20, 2011**

(54) COMPOSITION COMPRISING A LIPASE AND A BLEACH CATALYST

(75) Inventors: Philip Frank Souter, Northumberland (GB); Neil Joseph Lant, Newcastle Upon Tyne (GB); Alan Thomas Brooker, Newcastle Upon Tyne (GB); Gregory Scot Miracle, Hamilton, OH (US); Nicola Jane Binney, Newcastle Upon Tyne (GB); David Lee Daugherty, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 925 days.

This patent is subject to a terminal disclaimer.

(21) Appl. No.: 11/656,262

(22) Filed: Jan. 22, 2007

(65) Prior Publication Data

US 2007/0173429 A1 Jul. 26, 2007

Related U.S. Application Data

(60) Provisional application No. 60/761,114, filed on Jan. 23, 2006, provisional application No. 60/796,269, filed on Apr. 28, 2006, provisional application No. 60/854,840, filed on Oct. 26, 2006.

(51) Int. Cl.

| | |
|---|---|
| ***C11D 3/395*** | (2006.01) |
| ***C11D 3/39*** | (2006.01) |
| ***C11D 3/386*** | (2006.01) |
| ***C11D 3/34*** | (2006.01) |
| ***C12N 9/20*** | (2006.01) |

(52) U.S. Cl. ........ 510/374; 510/375; 510/376; 510/530; 510/392; 435/198

(58) Field of Classification Search ........................ None
See application file for complete search history.

(56) References Cited

U.S. PATENT DOCUMENTS

| | | | |
|---|---|---|---|
| 4,678,792 | A | 7/1987 | Nickl et al. |
| 5,045,223 | A | 9/1991 | Batal et al. |
| 5,047,163 | A | 9/1991 | Batal et al. |
| 5,360,568 | A | 11/1994 | Madison et al. |
| 5,360,569 | A | 11/1994 | Madison et al. |
| 5,370,826 | A | 12/1994 | Madison et al. |
| 5,442,066 | A | 8/1995 | Madison et al. |
| 5,478,357 | A | 12/1995 | Madison et al. |
| 5,482,515 | A | 1/1996 | Madison et al. |
| 5,550,256 | A | 8/1996 | Madison et al. |
| 5,576,282 | A | 11/1996 | Miracle et al. |
| 5,653,910 | A | 8/1997 | Kerschner et al. |
| 5,710,116 | A | 1/1998 | Miracle et al. |
| 5,753,599 | A | 5/1998 | Coope et al. |
| 5,760,222 | A | 6/1998 | Coope |
| 5,785,886 | A | 7/1998 | Kerschner et al. |
| 5,817,614 | A | 10/1998 | Miracle et al. |
| 5,869,438 | A | 2/1999 | Svendsen et al. |
| 5,952,282 | A | 9/1999 | Loffler et al. |
| 6,042,744 | A | 3/2000 | Nation et al. |
| 6,140,295 | A | 10/2000 | Behan et al. |
| 6,649,085 | B2 | 11/2003 | Reinhardt et al. |
| 6,939,702 | B1 | 9/2005 | Vind et al. |
| 2007/0173430 | A1 | 7/2007 | Souter et al. |
| 2007/0179074 | A1 | 8/2007 | Souter et al. |
| 2007/0179075 | A1 | 8/2007 | Souter et al. |
| 2007/0191247 | A1 | 8/2007 | Souter et al. |
| 2007/0191248 | A1 | 8/2007 | Souter et al. |
| 2007/0191249 | A1 | 8/2007 | Lant et al. |
| 2007/0191250 | A1 | 8/2007 | Lant et al. |

FOREIGN PATENT DOCUMENTS

| | | | |
|---|---|---|---|
| EP | 0 728 181 | B1 | 8/1996 |
| EP | 0 728 182 | B1 | 8/1996 |
| EP | 0 728 183 | B1 | 8/1996 |
| EP | 0 775 192 | B1 | 5/1997 |
| EP | 1 726 636 | A1 | 11/2006 |
| WO | WO 94/07984 | A1 | 4/1994 |
| WO | WO 95/00625 | A1 | 1/1995 |
| WO | WO 95/13351 | A1 | 5/1995 |
| WO | WO 95/13353 | A1 | 5/1995 |
| WO | WO 97/04078 | A1 | 2/1997 |
| WO | WO 97/04079 | A1 | 2/1997 |
| WO | WO 97/10323 | A1 | 3/1997 |
| WO | WO 98/16614 | A1 | 4/1998 |
| WO | WO 98/17767 | A1 | 4/1998 |
| WO | WO 99/42566 | A1 | 8/1999 |
| WO | WO 00/42151 | A1 | 7/2000 |
| WO | WO 00/42156 | A1 | 7/2000 |
| WO | WO 00/60063 | A1 | 10/2000 |
| WO | WO 01/16110 | A1 | 3/2001 |
| WO | WO 01/16263 | A2 | 3/2001 |
| WO | WO 01/16273 | A1 | 3/2001 |
| WO | WO 01/16274 | A1 | 3/2001 |

(Continued)

OTHER PUBLICATIONS

Cavicchioli, M. et al., "Oxyfunctionalization Reactions by Perfluora Cis-2, 3-dialkyloxaziridines. Enantioselective Conversion of Silanes Into Silanols," Tetrahedron Letters, vol. 35, No. 34, 1994, pp. 6329-6330.

Chiou, H., "A Method to Reduce the Radial Resistivity Gradient of (111) As-Grown Silicon Crystals," Motorola, Inc., Technical Developments, vol. 15, 1992, p. 120.

Davis, F., et al., "Chemistry of Oxaziridines. 13 Synthesis, Reactions, and Properties of 3-Substituted 1,2 Benzisothiazole 1,1-Dioxide Oxides," J. Org. Chemistry, vol. 55, 1990, pp. 1254-1261.

(Continued)

*Primary Examiner* — Rebecca Prouty

(74) *Attorney, Agent, or Firm* — Melissa G Krasovec; James F McBride; Leonard W Lewis

(57) ABSTRACT

The present invention relates to a composition comprising: (i) a lipase; and (ii) a bleach catalyst that is capable of accepting an oxygen atom from a peroxyacid and transferring the oxygen atom to an oxidizeable substrate.

9 Claims, No Drawings

FOREIGN PATENT DOCUMENTS

| | | | |
|---|---|---|---|
| WO | WO 01/16275 | A1 | 3/2001 |
| WO | WO 01/16276 | A1 | 3/2001 |
| WO | WO 01/16277 | A1 | 3/2001 |
| WO | WO 02/062973 | A2 | 8/2002 |
| WO | WO 2004/101759 | A2 | 11/2004 |
| WO | WO 2004/101760 | A2 | 11/2004 |
| WO | WO 2004/101763 | A2 | 11/2004 |
| WO | WO 2005/047264 | A1 | 5/2005 |
| WO | WO 2007/087258 | A2 | 8/2007 |

OTHER PUBLICATIONS

Hanquet, G., et al., "Peracid Oxidation of an Immonium Fluoroborate a New Example of Oxaziridium Salt," Tetrahedron Letters, vol. 28, No. 48, 1987, pp. 6061-6064.

Hanquet, G., et al., "Reaction of Paranitroperbenzoic Acid with N-Methyl-3, 4-Dihydroisoquinolinium Tetraflouroborate. Formation of an Oxaziridinium Salt," Tetrahedron, vol. 49, No. 2, 1993, pp. 423-438.

Jennings, W., et al., "Optically Active N-Phosphinoyloxaziridines: Preparation and Chiral Oxygen Transfer to Prochiral Sulfides," J. Chem. Soc. Chem Commun., 1994, pp. 2569-2570.

Mohamed, M., et al., "Experimental and Theoretical Studies on Pyrolysis of O-Acetyl Derivatives of B-Phenylcinnamaldehyde and Benzaldehyde Oximes," Polish J. Chem., vol. 77, 2003, pp. 577-590.

Van Ee, J., et al., "Application of Lipases in Detergents," Enzymes in Detergency, Chapters 6-7, 1997, pp. 93-132.

International Search Report in connection with PCT/US2007/001671, mailed on Jul. 4, 2007, pp. 1-5.

SEQUENCE LISTING

```
<160> NUMBER OF SEQ ID NOS: 2

<210> SEQ ID NO 1
<211> LENGTH: 807
<212> TYPE: DNA
<213> ORGANISM: Thermomyces lanuginosus
<220> FEATURE:
<221> NAME/KEY: CDS
<222> LOCATION: (1)..(807)
<220> FEATURE:
<221> NAME/KEY: mat_peptide
<222> LOCATION: (1)..()

<400> SEQUENCE: 1

gag gtc tcg cag gat ctg ttt aac cag ttc aat ctc ttt gca cag tat        48
Glu Val Ser Gln Asp Leu Phe Asn Gln Phe Asn Leu Phe Ala Gln Tyr
1               5                   10                  15

tct gca gcc gca tac tgc gga aaa aac aat gat gcc cca gct ggt aca        96
Ser Ala Ala Ala Tyr Cys Gly Lys Asn Asn Asp Ala Pro Ala Gly Thr
            20                  25                  30
```

-continued

```
aac att acg tgc acg gga aat gcc tgc ccc gag gta gag aag gcg gat       144
Asn Ile Thr Cys Thr Gly Asn Ala Cys Pro Glu Val Glu Lys Ala Asp
        35                  40                  45

gca acg ttt ctc tac tcg ttt gaa gac tct gga gtg ggc gat gtc acc       192
Ala Thr Phe Leu Tyr Ser Phe Glu Asp Ser Gly Val Gly Asp Val Thr
    50                  55                  60

ggc ttc ctt gct ctc gac aac acg aac aaa ttg atc gtc ctc tct ttc       240
Gly Phe Leu Ala Leu Asp Asn Thr Asn Lys Leu Ile Val Leu Ser Phe
65                  70                  75                  80

cgt ggc tct cgt tcc ata gag aac tgg atc ggg aat ctt aac ttc gac       288
Arg Gly Ser Arg Ser Ile Glu Asn Trp Ile Gly Asn Leu Asn Phe Asp
                85                  90                  95

ttg aaa gaa ata aat gac att tgc tcc ggc tgc agg gga cat gac ggc       336
Leu Lys Glu Ile Asn Asp Ile Cys Ser Gly Cys Arg Gly His Asp Gly
            100                 105                 110

ttc act tcg tcc tgg agg tct gta gcc gat acg tta agg cag aag gtg       384
Phe Thr Ser Ser Trp Arg Ser Val Ala Asp Thr Leu Arg Gln Lys Val
        115                 120                 125

gag gat gct gtg agg gag cat ccc gac tat cgc gtg gtg ttt acc gga       432
Glu Asp Ala Val Arg Glu His Pro Asp Tyr Arg Val Val Phe Thr Gly
    130                 135                 140

cat agc ttg ggt ggt gca ttg gca act gtt gcc gga gca gac ctg cgt       480
His Ser Leu Gly Gly Ala Leu Ala Thr Val Ala Gly Ala Asp Leu Arg
145                 150                 155                 160

gga aat ggg tat gat atc gac gtg ttt tca tat ggc gcc ccc cga gtc       528
Gly Asn Gly Tyr Asp Ile Asp Val Phe Ser Tyr Gly Ala Pro Arg Val
                165                 170                 175

gga aac agg gct ttt gca gaa ttc ctg acc gta cag acc ggc gga aca       576
Gly Asn Arg Ala Phe Ala Glu Phe Leu Thr Val Gln Thr Gly Gly Thr
            180                 185                 190

ctc tac cgc att acc cac acc aat gat att gtc cct aga ctc ccg ccg       624
Leu Tyr Arg Ile Thr His Thr Asn Asp Ile Val Pro Arg Leu Pro Pro
        195                 200                 205

cgc gaa ttc ggt tac agc cat tct agc cca gag tac tgg atc aaa tct       672
Arg Glu Phe Gly Tyr Ser His Ser Ser Pro Glu Tyr Trp Ile Lys Ser
    210                 215                 220

gga acc ctt gtc ccc gtc acc cga aac gat atc gtg aag ata gaa ggc       720
Gly Thr Leu Val Pro Val Thr Arg Asn Asp Ile Val Lys Ile Glu Gly
225                 230                 235                 240

atc gat gcc acc ggc ggc aat aac cag cct aac att ccg gat atc cct       768
Ile Asp Ala Thr Gly Gly Asn Asn Gln Pro Asn Ile Pro Asp Ile Pro
                245                 250                 255

gcg cac cta tgg tac ttc ggg tta att ggg aca tgt ctt                   807
Ala His Leu Trp Tyr Phe Gly Leu Ile Gly Thr Cys Leu
            260                 265
```

```
<210> SEQ ID NO 2
<211> LENGTH: 269
<212> TYPE: PRT
<213> ORGANISM: Thermomyces lanuginosus

<400> SEQUENCE: 2

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60
```

-continued

```
Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265
```

COMPOSITION COMPRISING A LIPASE AND A BLEACH CATALYST

CROSS-REFERENCES TO RELATED APPLICATIONS

This application claims priority under 35 U.S.C. §119(e) to U.S. Provisional Application Ser. No. 60/761,114 filed Jan. 23, 2006, U.S. Provisional Application Ser. No. 60/796,269 filed Apr. 28, 2006, and U.S. Provisional Application Ser. No. 60/854,840 filed Oct. 27, 2006.

FIELD OF THE INVENTION

The present invention relates to a composition comprising a lipase and a bleach catalyst. More specifically, the present invention relates to composition comprising a lipase and a bleach catalyst that is capable of accepting an oxygen atom from a peroxyacid and transferring the oxygen atom to an oxidizeable substrate. The compositions of the present invention are typically suitable for use as laundry detergent compositions and exhibit a good cleaning performance and a reduced malodor profile, especially on problematic residual dairy soils.

BACKGROUND OF THE INVENTION

Dingy soils such as body soils and other hydrophobic soils, including dairy soils, are extremely difficult to remove from fabric during a laundering process. The appearance of lipase enzymes suitable for detergent applications in the 1980's (e.g. Lipolase and Lipolase Ultra, ex Novo Nordisk—now Novozymes) gave the formulator a new approach to improve grease removal. Lipase enzymes catalyse the hydrolysis of triglycerides which form a major component of many commonly encountered fatty soils such as sebum, animal fats (e.g. lard, ghee, butter) and vegetable oils (e.g. olive oil, sunflower oil, peanut oil). However, these enzymes show limited performance in the first wash cycle (being effective mainly during the drying stage of the laundering process) and give rise to a post-wash malodor. Without wishing to be bound by theory, the malodor arises from fatty acids released by the hydrolysis of fats and is particularly noticeable for dairy soils like milk, cream, butter and yogurt; dairy fats contain triglycerides functionalized with short chain (e.g. $C_4$) fatty acyl units which release malodorous volatile fatty acids after lipolysis. For a general review of the use of lipases in solid laundry detergents see the following reference: Enzymes in Detergency, ed. J. H. van Ee et al, Vol 69 Marcel Dekker Surfactant Series, Marcel Dekker, New York, 1997, pp 93-132 (ISBN 0-8247-9995-X).

More recently so-called 'first wash' lipases have been commercialised such as Lipoprime™ and Lipex™ (ex. Novozymes) which show performance benefits in the initial wash cycle. The Lipex™ enzyme is described in more detail in WO 00/60063 and U.S. Pat. No. 6,939,702 B1 (Novozymes). Laundry detergent formulations comprising the Lipex™ enzyme are described in more detail in IP.com publication IP 6443D (Novozymes). However in order to better exploit lipase technology, both the odour profile on residual dairy stains and the cleaning performance on complex soils still needs to be improved.

Detergent manufacturers have also attempted to incorporate bleach catalysts, especially oxaziridium or oxaziridinium-forming bleach catalysts, in their detergent products in an attempt to provide a good bleaching performance. EP 0 728 181, EP 0 728 182, EP 0 728 183, EP 0 775 192, U.S. Pat.

No. 4,678,792, U.S. Pat. No. 5,045,223, U.S. Pat. No. 5,047,163, U.S. Pat. No. 5,360,568, U.S. Pat. No. 5,360,569, U.S. Pat. No. 5,370,826, U.S. Pat. No. 5,442,066, U.S. Pat. No. 5,478,357, U.S. Pat. No. 5,482,515, U.S. Pat. No. 5,550,256, U.S. Pat. No. 5,653,910, U.S. Pat. No. 5,710,116, U.S. Pat. No. 5,760,222, U.S. Pat. No. 5,785,886, U.S. Pat. No. 5,952,282, U.S. Pat. No. 6,042,744, WO95/13351, WO95/13353, WO97/10323, WO98/16614, WO00/42151, WO00/42156, WO01/16110, WO01/16263, WO01/16273, WO01/16274, WO01/16275, WO01/16276, WO01/16277 relate to detergent compositions comprising an oxaziriduium and/or an oxaziridinium-forming bleach catalyst.

There is a continuing need for laundry detergent compositions that exhibit a good overall cleaning profile, a good cold water temperature bleaching performance, good greasy soil cleaning performance and a reduced malodor profile on residual fatty soils, especially dairy soils.

The inventors have found that by using lipase in combination with a bleach catalyst that is capable of accepting an oxygen atom from a peroxyacid and transferring the oxygen atom to an oxidizeable substrate improves the cleaning performance of the detergent composition whilst maintaining a reduced malodor profile on residual fatty soils, especially dairy soils.

In another embodiment of the present invention, the inventors have found that the rubber sump hose compatibility profile is improved when a diacyl and/or a tetraacyl peroxide species is in combination with a lipase.

In an especially preferred embodiment of the present invention, the Inventors have found that using a lipase in combination with (i) a bleach catalyst that is capable of accepting an oxygen atom from a peroxyacid and transferring the oxygen atom to an oxidizeable substrate and (ii) a diacyl and/or tetraacyl peroxide species, significantly improves the cleaning performance of the composition, reduces the malodor profile of the composition and improves the rubber sump hose compatibility profile of the composition.

SUMMARY OF THE INVENTION

In a first embodiment, the present invention provides a composition comprising: (i) a lipase; and (ii) a bleach catalyst that is capable of accepting an oxygen atom from a peroxyacid and transferring the oxygen atom to an oxidizeable substrate.

In a second embodiment, the present invention provides a composition comprising: (i) a lipase; and (ii) a diacyl and/or tetraacyl peroxide species.

DETAILED DESCRIPTION OF THE INVENTION

Composition

The composition comprises: (i) a lipase; and (ii) a bleach catalyst that is capable of accepting an oxygen atom from a peroxyacid and transferring the oxygen atom to an oxidizeable substrate. The lipase and the bleach catalyst are described in more detail below.

The composition may be suitable for use as a laundry detergent composition, laundry additive composition, dishwashing composition, or hard surface cleaning composition. The composition is typically a detergent composition. The composition may be a fabric treatment composition. Preferably the composition is a laundry detergent composition.

The composition can be any form such as liquid or solid, although preferably the composition is in solid form. Typically, the composition is in particulate form such as an agglomerate, a spray-dried powder, an extrudate, a flake, a needle, a noodle, a bead, or any combination thereof. The composition may be in compacted particulate form, such as in the form of a tablet or bar. The composition may be in some other unit dose form, such as in the form of a pouch, wherein the composition is typically at least partially, preferably essentially completely, enclosed by a water-soluble film such as polyvinyl alcohol. Preferably, the composition is in free-flowing particulate form; by free-flowing particulate form, it is typically meant that the composition is in the form of separate discrete particles. The composition may be made by any suitable method including agglomeration, spray-drying, extrusion, mixing, dry-mixing, liquid spray-on, roller compaction, spheronisation, tabletting or any combination thereof.

The composition typically has a bulk density of from 450 g/l to 1,000 g/l, preferred low bulk density detergent compositions have a bulk density of from 550 g/l to 650 g/l and preferred high bulk density detergent compositions have a bulk density of from 750 g/l to 900 g/l. The composition may also have a bulk density of from 650 g/l to 750 g/l. During the laundering process, the composition is typically contacted with water to give a wash liquor having a pH of from above 7 to less than 13, preferably from above 7 to less than 10.5. This is the optimal pH to provide good cleaning whilst also ensuring a good fabric care profile.

Preferably, the composition comprises: (i) from 0% to less than 10%, preferably to 7%, or to 4%, or from 1%, or from 1.5%, by weight of the composition, of tetraacetylethylenediamine and/or oxybenzene sulphonate bleach activators. Most preferably, the composition is essentially free of tetraacetylethylenediamine and/or oxybenzene sulphonate bleach activators. By "is essential free of" it is typically meant "comprises no deliberately incorporated". Keeping the levels of these types of bleach activators to a minimum maintains the good dye safety profile of the composition.

Preferably, upon contact with water the composition forms a wash liquor having a pH of from 7 to 10.5. Compositions having this reserve alkalinity profile and pH profile exhibit a good stability profile for lipase.

Preferably, the composition comprises from 0% or from 1%, or from 2%, or from 3%, or from 4%, or from 5%, and to 30%, or to 20%, or to 10%, by weight of the composition, of a source of carbonate anion. The above described levels of a source of carbonate anion ensure that the composition has a good overall cleaning performance and a good bleaching performance.

Preferably, the composition comprises a dye transfer inhibitor. Suitable dye transfer inhibitors are selected from the group consisting of: polyvinylpyrrolidone, preferably having a weight average molecular weight of from 40,000 Da to 80,000 Da, preferably from 50,000 D1 to 70,000 Da; polyvinylimidazole, preferably having a weight average molecular weight of from 10,000 Da to 40,000 Da, preferably from 15,000 Da to 25,000 Da; polyvinyl pyridine N-oxide polymer, preferably having a weight average molecular weight of from 30,000 Da to 70,000 Da, preferably from 40,000 Da to 60,000 Da; a co-polymer of polyvinylpyrrolidone and vinyl imidazole, preferably having a weight average molecular weight of from 30,000 Da to 70,000 Da, preferably from 40,000 Da to 60,000 Da; and any combination thereof. Compositions comprising a dye transfer inhibitor show a further improved dye safety profile.

The composition may comprise from 0% to less than 5%, preferably to 4%, or to 3%, or to 2%, or even to 1%, by weight of the composition, of zeolite-builder. Whilst the composition may comprise zeolite-builder at a level of 5 wt % or greater, preferably the composition comprises less than 5 wt % zeolite-builder. It may be preferred for the composition to be essentially free of zeolite-builder. By: "essentially free of zeolite-builder", it is typically meant that the composition comprises no deliberately incorporated zeolite-builder. This is especially preferred when the composition is a solid laundry detergent composition and it is desirable for the composition to be very highly soluble, to minimize the amount of water-insoluble residues (for example, which may deposit on fabric surfaces), and also when it is highly desirable to have transparent wash liquor. Suitable zeolite-builders include zeolite A, zeolite X, zeolite P and zeolite MAP.

The composition may comprise from 0% to less than 10%, or less than 5%, preferably to 4%, or to 3%, or to 2%, or even to 1%, by weight of the composition, of phosphate-builder. Whilst the composition may comprise phosphate-builder at a level of 10 wt % or greater, preferably the composition comprises less than 10 wt % phosphate-builder. It may even be preferred for the composition to be essentially free of phosphate-builder. By: "essentially free of phosphate-builder", it is typically meant that the composition comprises no deliberately added phosphate-builder. This is especially preferred if it is desirable for the composition to have a very good environmental profile. Suitable phosphate-builders include sodium tripolyphosphate.

The composition may comprise from 0% to less than 5%, or preferably to 4%, or to 3%, or even to 2%, or to 1%, by weight of the composition, of silicate salt. Whilst the composition may comprise silicate salt at a level of 5 wt % or greater, preferably the composition comprises less than 5 wt % silicate salt. It may even be preferred for the composition to be essentially free of silicate salt. By: "essentially free from silicate salt", it is typically meant that the composition comprises no deliberately added silicate salt. This is especially preferred when the composition is a solid laundry detergent composition and it is desirable to ensure that the composition has very good dispensing and dissolution profiles and to ensure that the composition provides a clear wash liquor upon dissolution in water. The silicate salts include water-insoluble silicate salts. The silicate salts also include amorphous silicate salts and crystalline layered silicate salts (e.g. SKS-6). The silicate salts include sodium silicate.

The composition typically comprises adjunct ingredients. These adjunct ingredients include: detersive surfactants such as anionic detersive surfactants, non-ionic detersive surfactants, cationic detersive surfactants, zwitterionic detersive surfactants, amphoteric detersive surfactants; preferred anionic detersive surfactants are alkoxylated anionic detersive surfactants such as linear or branched, substituted or unsubstituted $C_{12-18}$ alkyl alkoxylated sulphates having an average degree of alkoxylation of from 1 to 30, preferably from 1 to 10, more preferably a linear or branched, substituted or unsubstituted $C_{12-18}$ alkyl ethoxylated sulphates having an average degree of ethoxylation of from 1 to 10, most preferably a linear unsubstituted $C_{12-18}$ alkyl ethoxylated sulphates having an average degree of ethoxylation of from 3 to 7, other preferred anionic detersive surfactants are alkyl sulphates, alkyl sulphonates, alkyl phosphates, alkyl phosphonates, alkyl carboxylates or any mixture thereof, preferred alkyl sulphates include linear or branched, substituted or unsubstituted $C_{10-18}$ alkyl sulphates, another preferred anionic detersive surfactant is a $C_{10-13}$ linear alkyl benzene sulphonate; preferred non-ionic detersive surfactants are $C_{8-18}$ alkyl alkoxylated alcohols having an average degree of alkoxylation of from 1 to 20, preferably from 3 to 10, most preferred are $C_{12-18}$ alkyl ethoxylated alcohols having an average degree of alkoxylation of from 3 to 10; preferred cationic detersive surfactants are mono-$C_{6-18}$ alkyl mono-hydroxy-ethyl di-methyl quaternary ammonium chlorides, more preferred are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride; source of peroxygen such as percarbonate salts and/or perborate salts, preferred is sodium percarbonate, the source of peroxygen is preferably at least partially coated, preferably completely coated, by a coating ingredient such as a carbonate salt, a sulphate salt, a silicate salt, borosilicate, or mixtures, including mixed salts thereof; bleach activators such as tetraacetyl ethylene diamine, oxybenzene sulphonate bleach activators such as nonanoyl oxybenzene sulphonate, caprolactam bleach activators, imide bleach activators such as N-nonanoyl-N-methyl acetamide; enzymes such as amylases, arabinases, xylanases, galactanases, glucanases, carbohydrases, cellulases, laccases, oxidases, peroxidases, proteases, glucanases, pectate lyases and mannanases, especially preferred are proteases; suds suppressing systems such as silicone based suds suppressors; fluorescent whitening agents; photobleach; filler salts such as sulphate salts, preferably sodium sulphate; fabric-softening agents such as clay, silicone and/or quaternary ammonium compounds, especially preferred is montmorillonite clay optionally in combination with a silicone; flocculants such as polyethylene oxide; dye transfer inhibitors such as polyvinylpyrrolidone, poly 4-vinylpyridine N-oxide and/or co-polymer of vinylpyrrolidone and vinylimidazole; fabric integrity components such as hydrophobically modified cellulose and oligomers produced by the condensation of imidazole and epichlorhydrin; soil dispersants and soil anti-redeposition aids such as alkoxylated polyamines and ethoxylated ethyleneimine polymers; anti-redeposition components such as carboxymethyl cellulose and polyesters; perfumes; sulphamic acid or salts thereof; citric acid or salts thereof; carbonate salts, especially preferred is sodium carbonate; and dyes such as orange dye, blue dye, green dye, purple dye, pink dye, or any mixture thereof.

A second embodiment of the present invention relates to a composition comprising: (i) a lipase, for example, a first cycle lipase; and (ii) a diacyl peroxide.

Lipase

The composition comprises a lipase. The incorporation of lipase into the composition improves the cleaning performance. In addition, the combination of the lipase with the bleach catalyst significantly reduces the malodor profile of the composition.

Typically, the lipase is an Enzyme Classification (EC) number 3.1.1, more especially 3.1.1.3 as defined by EC classification, IUPAC-IUBMB.

Preferably the composition comprises lipase in an amount of at least 0.5 mg, preferably at least 0.7 mg, or at least 1.0 mg, or at least 1.5 mg, or at least 2.0 mg, or even at least 3.0 mg, or at least 5.0 mg or even at least 10 mg of active lipase per 100 g of composition. The lipase may comprise a calcium binding site. The lipase may also show improved stability and/or activity, especially activity, in the presence of high levels of free calcium cations that may be present in the wash liquor. This is especially preferred when the composition comprises low levels of zeolite-builder and phosphate-builder.

Typical EC 3.1.1.3 lipases include those described in WO 00/60063, WO 99/42566, WO 97/04078, WO 97/04079, U.S. Pat. No. 5,869,438 and U.S. Pat. No. 6,939,702 B1. Preferred lipases are produced by *Absidia reflexa, Absidia corymbefera, Rhizmucor miehei, Rhizopus delemar, Aspergillus niger, Aspergillus tubigensis, Fusarium oxysporum, Fusarium heterosporum, Aspergillus oryzea, Penicilium camembertii, Aspergillus foetidus, Aspergillus niger, Thermomyces lanoginosus* (synonym: *Humicola lanuginosa*) and *Landerina penisapora*, particularly *Thermomyces lanoginosus*. Preferred lipases are supplied by Novozymes under the tradenames. Lipolase®, Lipolase Ultra®, Lipoprime® and Lipex® (registered tradenames of Novozymes) and LIPASE P "AMANO®" available from Areario Pharmaceutical Co. Ltd., Nagoya, Japan, AMANO-CES®, commercially available from Toyo Jozo Co., Tagata, Japan; and further *Chromobacter viscosum* lipases from U.S. Biochemical Corp., U.S.A. and Diosynth Co., Netherlands, and other lipases such as *Pseudomonas gladioli*. Other suitable lipases are described in WO 02062973, WO 2004/101759, WO 2004/101760 and WO 2004/101763.

Preferably, the lipase is a polypeptide having an amino acid sequence which: (a) has at least 90% identity with the wild-type lipase derived from *Humicola lanuginosa* strain DSM 4109; (b) compared to said wild-type lipase, comprises a substitution of an electrically neutral or negatively charged amino acid at the surface of the three-dimensional structure within 15 Å of E1 or Q249 with a positively charged amino acid; and/or (c) comprises a peptide addition at the C-terminal; and/or (d) comprises a peptide addition at the N-terminal; and/or (e) meets the following limitations: (i) comprises a negative amino acid in position E210 of said wild-type lipase; (ii) comprises a negatively charged amino acid in the region corresponding to positions 90-101 of said wild-type lipase; and (iii) comprises a neutral or negative amino acid at a position corresponding to N94 of said wild-type lipase and/or has a negative or neutral net electric charge in the region corresponding to positions 90-101 of said wild-type lipase. The peptide sequence of the wild-type lipase is given below (sequence I.D. No. 2).

In one embodiment, suitable lipases include the "first cycle lipases" described in WO 00/60063 and U.S. Pat. No. 6,939, 702 B1, preferably a variant of SEQ ID No. 2, more preferably a variant of SEQ ID No. 2 having at least 90% homology to SEQ ID No. 2 comprising a substitution of an electrically neutral or negatively charged amino acid with R or K at any of positions 3, 224, 229, 231 and 233, with a most preferred variant comprising T231R and N233R mutations, such most preferred variant being sold under the tradename Lipex®.

Other suitable lipases are cutinases and esterases.

Typically, the composition comprises lipase in an amount of from 10 LU/g to 20,000 LU/g, or from 100 LU/g to 10,000 LU/g, or even from 500 LU/g, or from 750 LU/g, and to 3,000 LU/g, or to 1,500 LU/g, or to 1,250 LU/g.

Bleach Catalyst

The bleach catalyst is capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof.

Suitable iminium cations and polyions include, but are not limited to, N-methyl-3,4-dihydroisoquinolinium tetrafluoroborate, prepared as described in Tetrahedron (1992), 49(2), 423-38 (see, for example, compound 4, p. 433); N-methyl-3, 4-dihydroisoquinolinium p-toluene sulphonate, prepared as described in U.S. Pat. No. 5,360,569 (see, for example, Column 11, Example 1); and N-octyl-3,4-dihydroisoquinolinium p-toluene sulphonate, prepared as described in U.S. Pat. No. 5,360,568 (see, for example, Column 10, Example 3).

Suitable iminium zwitterions include, but are not limited to, N-(3-sulfopropyl)-3,4-dihydroisoquinolinium, inner salt, prepared as described in U.S. Pat. No. 5,576,282 (see, for example, Column 31, Example II); N-[2-(sulphooxy)dodecyl]-3,4-dihydroisoquinolinium, inner salt, prepared as described in U.S. Pat. No. 5,817,614 (see, for example, Column 32, Example V); 2-[3-[(2-ethylhexyl)oxy]-2-(sulphooxy)propyl]-3,4-dihydroisoquinolinium, inner salt, prepared as described in WO05/047264 (see, for example, page 18, Example 8), and 2-[3-[(2-butyloctyl)oxy]-2-(sulphooxy)propyl]-3,4-dihydroisoquinolinium, inner salt.

Suitable modified amine oxygen transfer catalysts include, but are not limited to, 1,2,3,4-tetrahydro-2-methyl-1-isoquinolinol, which can be made according to the procedures described in Tetrahedron Letters (1987), 28(48), 6061-6064. Suitable modified amine oxide oxygen transfer catalysts include, but are not limited to, sodium 1-hydroxy-N-oxy-N-[2-(sulphooxy)decyl]-1,2,3,4-tetrahydroisoquinoline.

Suitable N-sulphonyl imine oxygen transfer catalysts include, but are not limited to, 3-methyl-1,2-benzisothiazole 1,1-dioxide, prepared according to the procedure described in the Journal of Organic Chemistry (1990), 55(4), 1254-61.

Suitable N-phosphonyl imine oxygen transfer catalysts include, but are not limited to, [R-(E)]-N-[(2-chloro-5-nitrophenyl)methylene]-P-phenyl-P-(2,4,6-trimethylphenyl)-phosphinic amide, which can be made according to the procedures described in the Journal of the Chemical Society, Chemical Communications (1994), (22), 2569-70.

Suitable N-acyl imine oxygen transfer catalysts include, but are not limited to, [N(E)]-N-(phenylmethylene)acetamide, which can be made according to the procedures described in Polish Journal of Chemistry (2003), 77(5), 577-590.

Suitable thiadiazole dioxide oxygen transfer catalysts include but are not limited to, 3-methyl-4-phenyl-1,2,5-thiadiazole 1,1-dioxide, which can be made according to the procedures described in U.S. Pat. No. 5,753,599 (Column 9, Example 2).

Suitable perfluoroimine oxygen transfer catalysts include, but are not limited to, (Z)-2,2,3,3,4,4,4-heptafluoro-N-(nonafluorobutyl)butanimidoyl fluoride, which can be made according to the procedures described in Tetrahedron Letters (1994), 35(34), 6329-30.

Suitable cyclic sugar ketone oxygen transfer catalysts include, but are not limited to, 1,2:4,5-di-O-isopropylidene-D-erythro-2,3-hexodiuro-2,6-pyranose as prepared in U.S. Pat. No. 6,649,085 (Column 12, Example 1).

Preferably, the bleach catalyst comprises an iminium and/or carbonyl functional group and is typically capable of forming an oxaziridinium and/or dioxirane functional group upon acceptance of an oxygen atom, especially upon acceptance of an oxygen atom from a peroxyacid and/or salt thereof. Preferably, the bleach catalyst comprises an oxaziridinium functional group and/or is capable of forming an oxaziridinium functional group upon acceptance of an oxygen atom, especially upon acceptance of an oxygen atom from a peroxyacid and/or salt thereof. Preferably, the bleach catalyst comprises a cyclic iminium functional group, preferably wherein the cyclic moiety has a ring size of from five to eight atoms (including the nitrogen atom), preferably six atoms. Preferably, the bleach catalyst comprises an aryliminium functional group, preferably a bi-cyclic aryliminium functional group, preferably a 3,4-dihydroisoquinolinium functional group. Typically, the imine functional group is a quaternary imine functional group and is typically capable of forming a quaternary oxaziridinium functional group upon acceptance of an oxygen atom, especially upon acceptance of an oxygen atom from a peroxyacid and/or salt thereof.

Preferably, the bleach catalyst has a chemical structure corresponding to the following chemical formula

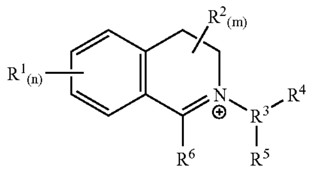

X wherein: n and m are independently from 0 to 4, preferably n and m are both 0; each $R^1$ is independently selected from a substituted or unsubstituted radical selected from the group consisting of hydrogen, alkyl, cycloalkyl, aryl, fused aryl, heterocyclic ring, fused heterocyclic ring, nitro, halo, cyano, sulphonato, alkoxy, keto, carboxylic, and carboalkoxy radicals; and any two vicinal $R^1$ substituents may combine to form a fused aryl, fused carbocyclic or fused heterocyclic ring; each $R^2$ is independently selected from a substituted or unsubstituted radical independently selected from the group consisting of hydrogen, hydroxy, alkyl, cycloalkyl, alkaryl, aryl, aralkyl, alkylenes, heterocyclic ring, alkoxys, arylcarbonyl groups, carboxyalkyl groups and amide groups; any $R^2$ may be joined together with any other of $R^2$ to form part of a common ring; any geminal $R^2$ may combine to form a carbonyl; and any two $R^2$ may combine to form a substituted or unsubstituted fused unsaturated moiety; $R^3$ is a $C_1$ to $C_{20}$ substituted or unsubstituted alkyl; $R^4$ is hydrogen or the moiety $Q_t$-A, wherein: Q is a branched or unbranched alkylene, t=0 or 1 and A is an anionic group selected from the group consisting of $OSO_3^-$, $SO_3^-$, $CO_2^-$, $OCO_2^-$, $OPO_3^{2-}$, $OPO_3H^-$ and $OPO_2^-$; $R^5$ is hydrogen or the moiety —$CR^{11}R^{12}$—Y-$G_b$-$Y_c$—[$(CR^9R^{10})_y$—O]$_k$—$R^8$, wherein: each Y is independently selected from the group consisting of O, S, N—H, or N—$R^8$; and each $R^8$ is independently selected from the group consisting of alkyl, aryl and heteroaryl, said moieties being substituted or unsubstituted, and whether substituted or unsubstituted said moieties having less than 21 carbons; each G is independently selected from the group consisting of CO, $SO_2$, SO, PO and $PO_2$; $R^9$ and $R^{10}$ are independently selected from the group consisting of H and $C_1$-$C_4$ alkyl; $R^{11}$ and $R^{12}$ are independently selected from the group consisting of H and alkyl, or when taken together may join to form a carbonyl; b=0 or 1; c can =0 or 1, but c must =0 if b=0; y is an integer from 1 to 6; k is an integer from 0 to 20; $R^6$ is H, or an alkyl, aryl or heteroaryl moiety; said moieties being substituted or unsubstituted; and X, if present, is a suitable charge balancing counterion, preferably X is present when $R^4$ is hydrogen, suitable X, include but are not limited to: chloride, bromide, sulphate, methosulphate, sulphonate, p-toluenesulphonate, borontetraflouride and phosphate.

In one embodiment of the present invention, the bleach catalyst has a structure corresponding to general formula below:

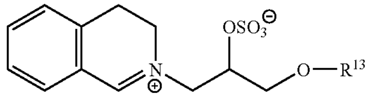

wherein $R^{13}$ is a branched alkyl group containing from three to 24 carbon atoms (including the branching carbon atoms) or a linear alkyl group containing from one to 24 carbon atoms; preferably $R^{13}$ is a branched alkyl group containing from eight to 18 carbon atoms or linear alkyl group containing from eight to eighteen carbon atoms; preferably $R^{13}$ is selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl; preferably $R^{13}$ is selected from the group consisting of 2-butyloctyl, 2-pentylnonyl, 2-hexyldecyl, iso-tridecyl and iso-pentadecyl.

Oxybenzene Sulphonate and/or Oxybenzoic Bleach Activators

The composition preferably comprises (i) oxybenzene sulphonate bleach activators and/or oxybenzoic bleach activators and (ii) a source of peroxygen. Typically, the oxybenzoic acid bleach activator is in its salt form. Preferred oxybenzene sulphonate bleach activators include bleach activators having the general formula:

R—(C═O)-L wherein R is an alkyl group, optionally branched, having, when the bleach activator is hydrophobic, from 6 to 14 carbon atoms, or from 8 to 12 carbon atoms and L is leaving group. Examples of suitable leaving groups are benzoic acid and derivatives thereof, especially salts thereof. Another especially preferred leaving group is oxybenzene sulphonate. Suitable bleach activators include dodecanoyl oxybenzene sulphonate, decanoyl oxybenzene sulphonate, a salt of decanoyl oxybenzoic acid, 3,5,5-trimethyl hexanoyloxybenzene sulphonate, nonanoylamidocaproyloxybenzene sulphonate, and nonanoyloxybenzene sulphonate (NOBS). Suitable bleach activators are also disclosed in WO 98/17767. The incorporation of these bleach activators into the composition is especially preferred when the composition comprises low levels of zeolite builder and phosphate builder. The inventors have found that combining these bleach activators with a source of peroxygen and a bleach catalyst as described in more detail above and a lipase, especially in an under-built detergent composition (such as a detergent composition comprising low levels of zeolite-builder and phosphate-builder), improves the overall cleaning performance, improves the rubber sump hose compatibility profile, and reduces the malodor profile of the composition.

Diacyl Peroxide

In another embodiment the composition comprises: (i) a lipase; and (ii) a diacyl and/or tetraacyl peroxide species. The Inventors have found that these composition exhibit excellent rubber hose compatibility. Diacyl peroxides and also tetraacyl peroxides are known to attack rubber, such as the rubber sump hoses of automatic washing machines, and over multiple washing cycles this can lead to failure of the rubber sump hose. The Inventors have found that combining the diacyl peroxides and/or tetraacyl peroxides with lipase overcomes this problem of rubber sump hose incompatibility.

The diacyl peroxide bleaching species is preferably selected from diacyl peroxides of the general formula:

$R^1$—C(O)—OO—(O)C—$R^2$ in which $R^1$ represents a $C_6$-$C_{18}$ alkyl, preferably $C_6$-$C_{12}$ alkyl group containing a linear chain of at least 5 carbon atoms and optionally containing one or more substituents (e.g. —$N^+(CH_3)_3$, —COOH or —CN) and/or one or more interrupting moieties (e.g. —CONH— or —CH═CH—) interpolated between adjacent carbon atoms of the alkyl radical, and $R^2$ represents an aliphatic group compatible with a peroxide moiety, such that $R^1$ and $R^2$ together contain a total of 8 to 30 carbon atoms. In one preferred aspect $R^1$ and $R^2$ are linear unsubstituted $C_6$-$C_{12}$ alkyl chains. Most preferably $R^1$ and $R^2$ are identical. Diacyl peroxides, in which both $R^1$ and $R^2$ are $C_6$-$C_{12}$ alkyl groups, are particularly preferred. Preferably, at least one of, most preferably only one of, the R groups ($R_1$ or $R_2$), does not contain branching or pendant rings in the alpha position, or preferably neither in the alpha nor beta positions or most preferably in none of the alpha or beta or gamma positions. In one further preferred embodiment the DAP may be asymmetric, such that preferably the hydrolysis of R1 acyl group is rapid to generate peracid, but the hydrolysis of R2 acyl group is slow.

The tetraacyl peroxide bleaching species is preferably selected from tetraacyl peroxides of the general formula:

$R^3$—C(O)—OO—C(O)—$(CH_2)n$-C(O)—OO—C(O)—$R^3$ in which $R^3$ represents a $C_1$-$C_9$ alkyl, preferably $C_3$-$C_7$, group and n represents an integer from 2 to 12, preferably 4 to 10 inclusive.

Preferably, the diacyl and/or tetraacyl peroxide bleaching species is present in an amount sufficient to provide at least 0.5 ppm, more preferably at least 10 ppm, and even more preferably at least 50 ppm by weight of the wash liquor. In a preferred embodiment, the bleaching species is present in an amount sufficient to provide from about 0.5 to about 300 ppm, more preferably from about 30 to about 150 ppm by weight of the wash liquor.

Pre-Formed Peroxyacid

The pre-formed peroxyacid or salt thereof is typically either a peroxycarboxylic acid or salt thereof, or a peroxysulphonic acid or salt thereof.

The pre-formed peroxyacid or salt thereof is preferably a peroxycarboxylic acid or salt thereof, typically having a chemical structure corresponding to the following chemical formula:

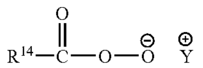

wherein: $R^{14}$ is selected from alkyl, aralkyl, cycloalkyl, aryl or heterocyclic groups; the $R^{14}$ group can be linear or branched, substituted or unsubstituted; and Y is any suitable counter-ion that achieves electric charge neutrality, preferably Y is selected from hydrogen, sodium or potassium. Preferably, $R^{14}$ is a linear or branched, substituted or unsubstituted $C_{6-9}$ alkyl. Preferably, the peroxyacid or salt thereof is selected from peroxyhexanoic acid, peroxyheptanoic acid, peroxyoctanoic acid, peroxynonanoic acid, peroxydecanoic acid, any salt thereof, or any combination thereof. Preferably, the peroxyacid or salt thereof has a melting point in the range of from 30° C. to 60° C.

The pre-formed peroxyacid or salt thereof can also be a peroxysulphonic acid or salt thereof, typically having a chemical structure corresponding to the following chemical formula:

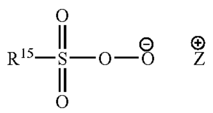

wherein: $R^{15}$ is selected from alkyl, aralkyl, cycloalkyl, aryl or heterocyclic groups; the $R^{15}$ group can be linear or branched, substituted or unsubstituted; and Z is any suitable counter-ion that achieves electric charge neutrality, preferably Z is selected from hydrogen, sodium or potassium. Preferably $R^{15}$ is a linear or branched, substituted or unsubstituted $C_{6-9}$ alkyl.

EXAMPLES

Example 1

Preparation of Sulphuric acid mono-[2-(3,4-dihydro-isoquinolin-2-yl)-1-(2-ethylhexyloxymethyl)-ethyl] ester, internal salt Preparation of 2-ethylhexyl glycidyl ether: To a flame dried, 500 mL round bottomed flask equipped with an addition funnel charged with epichlorohydrin (15.62 g, 0.17 moles), is added 2-ethylhexanol (16.5 g, 0.127 moles) and stannic chloride (0.20 g, 0.001 moles). The reaction is kept under an argon atmosphere and warmed to 90° C. using an oil bath. Epichlorohydrin is dripped into the stirring solution over 60 minutes followed by stirring at 90° C. for 18 hours. The reaction is fitted with a vacuum distillation head and 1-chloro-3-(2-ethyl-hexyloxy)-propan-2-ol is distilled under 0.2 mm Hg. The 1-chloro-3-(2-ethyl-hexyloxy)-propan-2-ol (4.46 g, 0.020 moles) is dissolved in tetrahydrofuran (50 mL) and stirred at room temperature under an argon atmosphere. To the stirring solution is added potassium tert-butoxide (2.52 g, 0.022 moles) and the suspension is stirred at room temperature for 18 hours. The reaction is then evaporated to dryness, residue dissolved in hexanes and washed with water (100 mL). The hexanes phase is separated, dried with $Na_2SO_4$, filtered and evaporated to dryness to yield the crude 2-ethylhexyl glycidyl ether, which can be further purified by vacuum distillation.

Preparation of Sulphuric acid mono-[2-(3,4-dihydro-isoquinolin-2-yl)-1-(2-ethylhexyloxymethyl)-ethyl]ester, internal salt: To a flame dried 250 mL three neck round bottomed flask, equipped with a condenser, dry argon inlet, magnetic stir bar, thermometer, and heating bath is added 3,4-dihydroisoquinoline (0.40 mol.; prepared as described in Example I of U.S. Pat. No. 5,576,282), 2-ethylhexyl glycidyl ether (0.38 mol, prepared as described above), $SO_3$-DMF complex (0.38 mol), and acetonitrile (500 mL). The reaction is warmed to 80° C. and stirred at temperature for 72 hours. The reaction is cooled to room temperature, evaporated to dryness and the residue recrystallized from ethyl acetate and/or ethanol to yield the desired product. The solvent acetonitrile may be replaced with other solvents, including but not limited to, 1,2-dichloroethane.

Example 2

Preparation of Sulphuric acid mono-[2-(3,4-dihydro-isoquinolin-2-yl)-1-(2-butyl-octyloxymethyl)-ethyl] ester, internal salt The desired product is prepared according to Example 1 but substituting 2-butyloctanol for 2-hexyloctanol.

Example 3

Laundry Detergent Compositions

The following laundry detergent compositions A, B, C and D are suitable for use in the present invention. Typically, these compositions are dosed into water at a concentration of from 80 g/l to 120 g/l during the laundering process.

| Ingredient | A | B | C | D |
|---|---|---|---|---|
| Bleach catalyst made according to example 1 or 2 | 0.1 wt % | 0.05 wt % | 0.03 wt % | 0.05 wt % |
| Lipase (9 mg/g active) | 0.15 wt % | 0.2 wt % | 0.3 wt % | 0.2 wt % |
| Sodium linear $C_{12-13}$ alkyl benzenesulphonate (LAS) | 9.0 wt % | 8 wt % | 7.5 wt % | 7.0 wt % |
| Tallow alkyl sulphate (TAS) | 1.0 wt % | 1.0 wt % | | |
| $C_{14-15}$ alkyl ethoxylated alcohol having an average degree of ethoxylation of 7 (AE7) | 2.5 wt % | | | |
| $C_{14-15}$ alkyl ethoxylated alcohol sulphate having an average degree of ethoxylation of 3 ($AE_3S$) | | 4 wt % | 3.0 wt % | 2.5 wt % |
| Mono-$C_{12-14}$ alkyl mono-hydroxyethyl di-methyl quaternary ammonium chloride | 1.5 wt % | 1.0 wt % | | |
| Zeolite 4A | 15 wt % | 12.5 wt % | | |
| Citric Acid | 3.0 wt % | 2.0 wt % | 3.0 wt % | 3.0 wt % |
| Sodium Percarbonate | 20 wt % | 15 wt % | 17.5 wt % | 14 wt % |
| TAED (tetraacetylethylenediamine) | 2.5 wt % | 3 wt % | 2.3 wt % | 1.6 wt % |
| NOBS (nonanoyloxybenzene sulphonate) | 0.0% | 1.0 wt % | 0.0 wt % | 1.5 wt % |
| Sodium carbonate | 20 wt % | 25 wt % | 20 wt % | 25 wt % |
| Polymeric carboxylate | 2.0 wt % | 1.5 wt % | 3.0 wt % | 2.5 wt % |
| A compound having the following general structure: bis(($C_2H_5O$)($C_2H_4O$)n)($CH_3$)—$N^+$—$C_xH_{2x}$—$N^+$—($CH_3$)—bis(($C_2H_5O$)($C_2H_4O$)n), wherein n = from 20 to 30, and x = from 3 to 8, or sulphated or sulphonated variants thereof | 1.0 wt % | 0.5 wt % | 0.75 t % | 1.0 wt % |
| Carboxymethyl cellulose | | | 1.5 wt % | 1.0 wt % |
| Other enzymes | 1.0 wt % | 0.5 wt % | 0.75 wt % | 0.5 wt % |
| Ethylene diamine disuccinic acid | 0.5 wt % | 0.1 wt % | 0.2 wt % | 0.25 wt % |
| Magnesium sulphate | 0.75 wt % | 0.5 wt % | 1.0 wt % | 0.5 wt % |

-continued

| Ingredient | A | B | C | D |
|---|---|---|---|---|
| Hydroxyethane di(methylene phosphonic acid) | 0.5 wt % | 0.25 wt % | 0.2 wt % | 0.4 wt % |
| Fluorescent whitening agent | 0.2 wt % | 0.1 wt % | 0.15 wt % | 0.25 wt % |
| Silicone suds suppressing agent | 0.1 wt % | 0.05 wt % | 0.1 wt % | 0.1 wt % |
| Soap | 0.5 wt % | 0.25 wt % | 0.0 wt % | 0.3 wt % |
| Photobleach | 0.01 wt % | 0.0001 wt % | 0.0005 wt % | 0.0015 wt % |
| Perfume | 1.0 wt % | 0.5 wt % | 0.75 wt % | 0.5 wt % |
| Sodium sulphate | 13 wt % | 15 wt % | 30 wt % | 30 wt % |
| Water and miscellaneous | to 100 wt % | to 100 wt % | to 100 wt % | to 100 wt % |

The following laundry detergent compositions E, F, G and H are suitable for use in the present invention. Typically, these compositions are dosed into water at a concentration of from 80 g/l to 120 g/l during the laundering process.

| Ingredient | E | F | G | H |
|---|---|---|---|---|
| Bleach catalyst made according to example 1 or 2 | | | 0.01 wt % | 0.05 wt % |
| Diacyl peroxide | 2 wt % | 1 wt % | 0.5 wt % | 1 wt % |
| Lipase (9 mg/g active enzyme) | 0.5 wt % | 0.3 wt % | 0.2 wt % | 0.1 wt % |
| Sodium linear $C_{12-13}$ alkyl benzenesulphonate (LAS) | 8.0 wt % | 5.0 wt % | 7.5 wt % | 7.0 wt % |
| $C_{14-15}$ alkyl ethoxylated alcohol sulphate having an average degree of ethoxylation of 3 ($AE_3S$) | 5.0 wt % | 2.5 wt % | 3.5 wt % | 6.0 wt % |
| Citric Acid | 3.0 wt % | 2.0 wt % | 5.0 wt % | 2.5 wt % |
| Sodium carbonate | 20 wt % | 25 wt % | 22.5 wt % | 25 wt % |
| Polymeric carboxylate | 2.0 wt % | 3.5 wt % | 3.5 wt % | 2.5 wt % |
| A compound having the following general structure: bis($(C_2H_5O)(C_2H_4O)n)(CH_3)—N^+—C_xH_{2x}—N^+—(CH_3)—$ bis($(C_2H_5O)(C_2H_4O)n$), wherein n = from 20 to 30, and x = from 3 to 8, or sulphated or sulphonated variants thereof | 1.0 wt % | 0.5 wt % | 0.75 wt % | 1.0 wt % |
| Sodium Percarbonate | 0 wt % | 15 wt % | 17.5 wt % | 14 wt % |
| TAED (tetraacetylethylenediamine) | 0 wt % | 3 wt % | 2.3 wt % | 1.6 wt % |
| Carboxymethyl cellulose | 0.5 wt % | 1.0 wt % | 1.5 wt % | 1.0 wt % |
| Other Enzymes | 1.0 wt % | 0.5 wt % | 0.2 wt % | 0.5 wt % |
| Ethylene diamine disuccinic acid | 0.05 wt % | 0.1 wt % | 0.2 wt % | 0.15 wt % |
| Magnesium sulphate | 0.35 wt % | 0.1 wt % | 1.0 wt % | 0.25 wt % |
| Hydroxyethane di(methylene phosphonic acid) | 0.1 wt % | 0.25 wt % | 0.2 wt % | 0.5 wt % |
| Fluorescent whitening agent | 0.2 wt % | 0.1 wt % | 0.15 wt % | 0.25 wt % |
| Silicone suds suppressing agent | 0.1 wt % | 0.05 wt % | 0.1 wt % | 0.2 wt % |
| Soap | 0.5 wt % | 0.25 wt % | 1.0 wt % | 0.5 wt % |
| Photobleach | 0.01 wt % | 0.0001 wt % | 0.0005 wt % | 0.0015 wt % |
| Perfume | 1.0 wt % | 0.5 wt % | 0.75 wt % | 0.5 wt % |
| Sodium sulphate | 45 wt % | 30 wt % | 20 wt % | 22 wt % |
| Water and miscellaneous | to 100 wt % | to 100 wt % | to 100 wt % | to 100 wt % |

The following laundry detergent compositions I, J, K and L are suitable for use in the present invention. Typically, these compositions are dosed into water at a concentration of from 20 g/l to 60 g/l during the laundering process.

| Ingredient | I | J | K | L |
|---|---|---|---|---|
| Bleach catalyst made according to example 1 or 2 | 0.15 wt % | 0.10 wt % | 0.1 wt % | 0.15 wt % |
| Diacyl peroxide | | | 1 wt % | 0.5 wt % |
| Lipase | 0.5 wt % | 0.3 wt % | 0.1 wt % | 0.2 wt % |
| Sodium linear $C_{12-13}$ alkyl benzenesulphonate (LAS) | 15 wt % | 17.5 wt % | 20 wt % | 10.0 wt % |

-continued

| Ingredient | I | J | K | L |
|---|---|---|---|---|
| $C_{14-15}$ alkyl ethoxylated alcohol sulphate having an average degree of ethoxylation of 3 ($AE_3S$) | 7.0 wt % | 7.5 wt % | 5.0 wt % | 5.0 wt % |
| Citric Acid | 7.0 wt % | 5.0 wt % | 7.5 wt % | 3.0 wt % |
| Sodium Percarbonate | 20 wt % | 15 wt % | 0 wt % | 14 wt % |
| TAED (tetraacetylethylenediamine) | 2.5 wt % | 3 wt % | 0 wt % | 1.6 wt % |
| NOBS (nonanoyloxybenzene sulphonate) | 0.0 wt % | 2.0 wt % | 0.0 wt % | 0 wt % |
| Sodium carbonate | 22.5 wt % | 25 wt % | 20 wt % | 10 wt % |
| Polymeric carboxylate | 7.0 wt % | 7.5 wt % | 5.0 wt % | 3.0 wt % |
| A compound having the following general structure: $bis((C_2H_5O)(C_2H_4O)n)(CH_3)—N^+—C_xH_{2x}—N^+—(CH_3)—bis((C_2H_5O)(C_2H_4O)n)$, wherein n = from 20 to 30, and x = from 3 to 8, or sulphated or sulphonated variants thereof | 2.5 wt % | 1.5 wt % | 3.0 wt % | 1.0 wt % |
| Carboxymethyl cellulose | 2.5 wt % | 3.0 wt % | 1.5 wt % | 1.0 wt % |
| Other Enzymes | 2.5 wt % | 1.5 wt % | 3.0 wt % | 0.75 wt % |
| Ethylene diamine disuccinic acid | 0.25 wt % | 0.1 wt % | 0.5 wt % | 0.15 wt % |
| Hydroxyethane di(methylene phosphonic acid) | 0.5 wt % | 0.75 wt % | 0.25 wt % | 0.2 wt % |
| Fluorescent whitening agent | 0.5 wt % | 0.75 wt % | 0.25 wt % | 0.15 wt % |
| Silicone suds suppressing agent | 0.05 wt % | 0.10 wt % | 0.02 wt % | 0.02 wt % |
| Photobleach | 0.025 wt % | 0.050 wt % | 0.02 wt % | 0.0015 wt % |
| Water, filler (including sodium sulphate) and miscellaneous | to 100 wt % | to 100 wt % | to 100 wt % | to 100 wt % |

Bleaching detergent compositions having the form of granular laundry detergents are exemplified by the following formulations. Any of the below compositions is used to launder fabrics at a concentration of 600-10000 ppm in water, with typical median conditions of 2500 ppm, 25° C., and a 25:1 water:cloth ratio. The typical pH is about 10 but can be can be adjusted by altering the proportion of acid to Na-salt form of alkylbenzenesulfonate.

| | M | N | O | P | Q | R |
|---|---|---|---|---|---|---|
| Linear alkylbenzenesulfonate | 20 | 22 | 20 | 15 | 20 | 20 |
| $C_{12}$ Dimethylhydroxyethyl ammonium chloride | 0.7 | 1 | 0.0 | 0.6 | 0.0 | 0.7 |
| AE3S | 0.9 | 0.0 | 0.9 | 0.0 | 0.0 | 0.9 |
| AE7 | 0.0 | 0.5 | 0.0 | 1 | 3 | 1 |
| sodium tripolyphosphate | 23 | 30 | 23 | 17 | 12 | 23 |
| Zeolite A | 0.0 | 0.0 | 0.0 | 0.0 | 10 | 0.0 |
| 1.6R Silicate | 7 | 7 | 7 | 7 | 7 | 7 |
| Sodium Carbonate | 15 | 14 | 15 | 18 | 15 | 15 |
| Polyacrylate MW 4500 | 1 | 0.0 | 1 | 1 | 1.5 | 1 |
| Carboxy Methyl Cellulose | 1 | 1 | 1 | 1 | 1 | 1 |
| Savinase 32.89 mg/g | 0.1 | 0.07 | 0.1 | 0.1 | 0.1 | 0.1 |
| Natalase 8.65 mg/g | 0.1 | 0.1 | 0.1 | 0.0 | 0.1 | 0.1 |
| Lipase 18 mg/g* | 0.03 | 0.07 | 0.3 | 0.1 | 0.07 | 0.1 |
| Tinopal AMS (ex. Ciba) | 0.06 | 0.0 | 0.06 | 0.18 | 0.06 | 0.06 |
| Tinopal CBS-X (ex. Ciba) | 0.1 | 0.06 | 0.1 | 0.0 | 0.1 | 0.1 |
| Diethylenetriamine pentacetic acid | 0.6 | 0.3 | 0.6 | 0.25 | 0.6 | 0.6 |
| $MgSO_4$ | 1 | 1 | 1 | 0.5 | 1 | 1 |
| Sodium Percarbonate | 0.0 | 5.2 | 0.1 | 0.0 | 0.0 | 0.0 |
| Photobleach | 0.0030 | 0.0015 | 0.0015 | 0.0020 | 0.0045 | 0.0010 |
| Sodium Perborate Monohydrate | 4.4 | 0.0 | 3.85 | 2.09 | 0.78 | 3.63 |
| NOBS | 1.9 | 0.0 | 1.66 | 0.0 | 0.33 | 0.75 |
| TAED | 0.58 | 1.2 | 0.51 | 0.0 | 0.015 | 0.28 |
| Organic Catalyst** | 0.0185 | 0.0185 | 0.0162 | 0 | 0.0111 | 0.0074 |
| Diacyl peroxide*** | | 0.5 | | 1 | | |
| Sulfate/Moisture | Balance to 100% | Balance to 100% | Balance to 100% | Balance to 100% | Balance to 100% | Balance to 100% |

*Lipase is preferably Lipex ®.

**Organic catalyst prepared according to Examples 1 or 2 or mixtures thereof.

***Diacyl peroxide is preferably dinonanoylperoxide.

Sequence I.D No. 2

```
Glu Val Ser Gln Asp Leu Phe Asn Gln Phe Asn Leu
1               5                   10
Phe Ala Gln Tyr
        15

Ser Ala Ala Ala Tyr Cys Gly Lys Asn Asn Asp Ala
            20                  25
Pro Ala Gly Thr
    30

Asn Ile Thr Cys Thr Gly Asn Ala Cys Pro Glu Val
        35                  40
Glu Lys Ala Asp
45

Ala Thr Phe Leu Tyr Ser Phe Glu Asp Ser Gly Val
     50                 55                   60
Gly Asp Val Thr

Gly Phe Leu Ala Leu Asp Asn Thr Asn Lys Leu Ile
65                  70                  75
Val Leu Ser Phe
            80

Arg Gly Ser Arg Ser Ile Glu Asn Trp Ile Gly Asn
                85                  90
Leu Asn Phe Asp
         95

Leu Lys Glu Ile Asn Asp Ile Cys Ser Gly Cys Arg
            100                 105
Gly His Asp Gly
    110

Phe Thr Ser Ser Trp Arg Ser Val Ala Asp Thr Leu
        115                 120
Arg Gln Lys Val
125

Glu Asp Ala Val Arg Glu His Pro Asp Tyr Arg Val
    130                 135                 140
Val Phe Thr Gly

His Ser Leu Gly Gly Ala Leu Ala Thr Val Ala Gly
145                 150                 155
Ala Asp Leu Arg
            160
```

-continued

```
Gly Asn Gly Tyr Asp Ile Asp Val Phe Ser Tyr Gly
                165                 170
Ala Pro Arg Val
        175

Gly Asn Arg Ala Phe Ala Glu Phe Leu Thr Val Gln
            180                 185
Thr Gly Gly Thr
    190

Leu Tyr Arg Ile Thr His Thr Asn Asp Ile Val Pro
        195                 200
Arg Leu Pro Pro
205

Arg Glu Phe Gly Tyr Ser His Ser Ser Pro Glu Tyr
    210                 215                 220
Trp Ile Lys Ser

Gly Thr Leu Val Pro Val Thr Arg Asn Asp Ile Val
225                 230                 235
Lys Ile Glu Gly
            240

Ile Asp Ala Thr Gly Gly Asn Asn Gln Pro Asn Ile
                245                 250
Pro Asp Ile Pro
        255

Ala His Leu Trp Tyr Phe Gly Leu Ile Gly Thr Cys
            260                 265
Leu
```

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A composition comprising:

(a) a lipase, wherein the lipase is a polypeptide having an amino acid sequence which: has at least 90% identity with the wild-type lipase derived from *Humicola lanuginosa* strain DSM 4109; and compared to said wild-type lipase, comprises a substitution of an electrically neutral or negatively charged amino acid at the surface of the three-dimensional structure within 15 Å of E1 or Q249 with a positively charged amino acid; and (b) a bleach catalyst that is capable of accepting an oxygen atom from a peroxyacid and transferring the oxygen atom to an oxidizeable substrate, wherein the bleach catalyst has a chemical structure corresponding to the chemical formula:

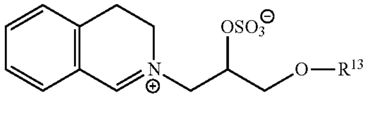

wherein $R^{13}$ is a branched alkyl group containing from 3 to 24 carbons, or a linear alkyl group containing from 1 to 24 carbons.

2. A composition according to claim 1, wherein the bleach catalyst has a chemical structure corresponding to the chemical formula:

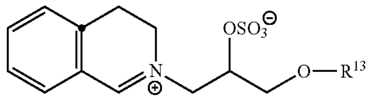

wherein $R^{13}$ is selected from the group consisting of 2-butyloctyl, 2-pentylnonyl, 2-hexyldecyl, iso-tridecyl and iso-pentadecyl.

3. A composition according to claim 1, wherein the lipase is a variant of the *Humicola lanuginosa* lipase with the mutations T231R and N233R.

4. A composition according to claim 1, wherein the composition comprises less than 5%, by weight of the composition, of a source of peroxygen.

5. A composition according to claim 1, wherein the composition comprises from 5% to 10%, by weight of the composition, of a source of carbonate anion.

6. A composition according to claim 1, wherein the composition comprises a dye transfer inhibitor.

7. A composition according to claim 1, wherein the composition comprises:

(a) less than 5%, by weight of the composition, of zeolite builder;

(b) optionally, less than 5%, by weight of the composition, of phosphate builder; and (c) optionally, less than 5%, by weight of the composition, of silicate salt.

8. A composition according to claim 1, wherein the composition comprises a diacyl and/or a tetraacyl peroxide species.

9. A composition according to claim 1, wherein the composition comprises a pre-formed peroxyacid.

* * * * *